US012723961B2

(12) United States Patent
Gallinger et al.

(10) Patent No.: US 12,723,961 B2
(45) Date of Patent: Sep. 1, 2026

(54) TEMPERATURE CONTROL SYSTEM FOR A DIFFUSION CELL, DIFFUSION CELL, DIFFUSION CELL SYSTEM, AND METHOD FOR CONTROLLING THE TEMPERATURE IN A DIFFUSION CELL

(71) Applicant: LTS Lohmann Therapie-Systeme AG, Andemach (DE)

(72) Inventors: Helena Gallinger, Andemach (DE); Andreas Koch, Melsbach (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 322 days.

(21) Appl. No.: 18/037,227

(22) PCT Filed: Nov. 17, 2021

(86) PCT No.: PCT/EP2021/081959
§ 371 (c)(1),
(2) Date: May 16, 2023

(87) PCT Pub. No.: WO2022/106453
PCT Pub. Date: May 27, 2022

(65) Prior Publication Data

US 2023/0417642 A1 Dec. 28, 2023

(30) Foreign Application Priority Data

Nov. 18, 2020 (DE) .................... 10 2020 130 492.7

(51) Int. Cl.

| | |
|---|---|
| ***G01N 13/00*** | (2006.01) |
| *F28D 1/06* | (2006.01) |
| *G01N 33/15* | (2006.01) |

(52) U.S. Cl.
CPC ............... *G01N 13/00* (2013.01); *F28D 1/06* (2013.01); *G01N 2013/003* (2013.01); *G01N 33/15* (2013.01)

(58) Field of Classification Search
CPC .......... G01N 1/44; G01N 13/00; G01N 33/15; G01N 2013/003; G01N 2035/00178; F28D 1/06
See application file for complete search history.

(56) References Cited

U.S. PATENT DOCUMENTS 4,594,884 A * 6/1986 Bondi .................... G01N 13/00 435/287.1
5,296,139 A * 3/1994 Hanson .................. G01N 13/00 210/321.63

(Continued)

FOREIGN PATENT DOCUMENTS

DE 102017128269 A1 * 5/2019 ............ G01N 13/00
WO 2016162481 A1 10/2016

OTHER PUBLICATIONS

Machine Translation of DE 102017128269 (Year: 2019).*

(Continued)

*Primary Examiner* — Nathaniel J Kolb
(74) *Attorney, Agent, or Firm* — The Webb Law Firm

(57) ABSTRACT

A temperature control system for a diffusion cell. The temperature control system includes a cell head and a temperature control device connected to the cell head. Moreover, a diffusion cell having such a temperature control system. Furthermore a diffusion cell system having such a temperature control system or such a diffusion cell. Finally, a method for controlling the temperature of a cell head of a diffusion cell, including introducing the temperature control fluid into the cell head.

23 Claims, 7 Drawing Sheets

(56) References Cited

U.S. PATENT DOCUMENTS

| | | | | |
|---|---|---|---|---|
| 5,694,196 | A * | 12/1997 | Hirai | G01N 13/00 351/200 |
| 5,789,240 | A * | 8/1998 | Abdulrazik | G01N 33/15 435/284.1 |
| 11,364,153 | B2 | 6/2022 | Klaffenbach | |
| 2003/0144626 | A1* | 7/2003 | Hanson | G01N 13/00 604/73 |
| 2003/0170610 | A1* | 9/2003 | Cima | G01N 33/5088 435/297.5 |
| 2008/0206211 | A1 | 8/2008 | Gueniche | |
| 2010/0071445 | A1* | 3/2010 | Kamiyama | G01N 13/00 73/64.47 |
| 2012/0167671 | A1* | 7/2012 | Mikulasik | B01D 29/48 73/61.52 |
| 2012/0324984 | A1* | 12/2012 | Wakefield | G01N 3/12 73/38 |
| 2013/0085105 | A1 | 4/2013 | Deasy et al. | |
| 2014/0102177 | A1* | 4/2014 | Kang | G01N 33/15 73/38 |
| 2017/0232059 | A1 | 8/2017 | Uvnäs-Moberg | |
| 2018/0259438 | A1* | 9/2018 | Munt | G01N 13/00 |
| 2020/0064247 | A9* | 2/2020 | Munt | G01N 13/00 |

OTHER PUBLICATIONS

Franz, "Percutaneous Absorption on the Relevance of In Vitro Data", The Journal of Investigative Dermatology, 1975, pp. 190-195, vol. 64, No. 3.

US Food and Drug Administration, Draft Guidance on "Transdermal and Topical Delivery Systems—Product Development and Quality Considerations", Nov. 2019.

* cited by examiner 28
24
16
30
18
20
12
32
17
22
34
14
26
100

TEMPERATURE CONTROL SYSTEM FOR A DIFFUSION CELL, DIFFUSION CELL, DIFFUSION CELL SYSTEM, AND METHOD FOR CONTROLLING THE TEMPERATURE IN A DIFFUSION CELL

CROSS-REFERENCE TO RELATED APPLICATIONS

This application is the United States national phase of International Application No. PCT/EP2021/081959 filed Nov. 17, 2021, and claims priority to German Patent Application No. 10 2020 130 492.7 filed Nov. 18, 2020, the disclosures of which are hereby incorporated by reference in their entireties.

BACKGROUND OF THE INVENTION

Field of the Invention

The present invention relates to a temperature control system for a diffusion cell, a diffusion cell, a diffusion cell system, and a method for controlling the temperature of a cell head of a diffusion cell.

Description of Related Art

In vitro permeation studies are conducted to evaluate the performance of dermal dosage forms, such as ointments or creams, in particular of transdermal therapeutic systems (US).

A standard for conducting such in vitro skin permeation studies, in particular for the examination of US, is the use of the so-called FRANZ diffusion cell (Thomas Franz; J. of Invest. Dermatology, 64:190-195, 1975). Exemplary embodiments of this diffusion cell are shown in FIGS. 1 and 2.

FIG. 1 shows a diffusion cell 100 according to prior art with a static and vertical structure. Substantially, diffusion cell 100 consists of two different compartments, on the one hand the donor compartment, also called donor chamber 12, and on the other hand the acceptor compartment, also called acceptor chamber 14, which are spatially separated from each other by a diffusion membrane 16. The donor chamber 12 shown has a substantially hollow cylindrical chamber 18 with access opening 20 in the upper region. The diffusion membrane 16 preferably comprises skin, for example human or animal skin, in particular consists thereof. Donor chamber 12 and acceptor chamber 14 with diffusion membrane 16 therebetween are connected to each other in a form-fitting manner, in particular screwed together, via a retaining clip 22. On surface side 17 of diffusion membrane 16 facing the donor chamber, the dermal dosage form, in this case designed as TTS 32, for example, is arranged or applied, respectively. Instead of the TTS, other dosage forms, in particular semi-solid galenic dosage forms, such as ointments or creams or even liquids can be applied.

During the experiment, components of the dermal dosage form, in particular active ingredient components, penetrate diffusion membrane 16 and mix with medium 34, such as a salt solution, in acceptor chamber 14. This penetration or permeation through diffusion membrane 16 is exemplary shown by arrow 30 in FIG. 1. By means of a magnetic rotating rod 26, medium 34 can be mixed. A sampling of medium 34 is possible through sampling device 24 which is designed as a tube. It is possible that the temperature of medium 34 in acceptor chamber 14 is controlled, for example to 32° C., in particular via an acceptor chamber temperature control device, for example via a temperature control bath 28.

FIG. 2 is a perspective illustration of a further embodiment of a diffusion cell 100 based substantially on the embodiment of FIG. 1. The retaining clip 22 has two locking screws 23 for a tightened, detachable form-fitting connection between donor chamber 12 and acceptor chamber 14.

Usually, donor chamber 12 is at the room temperature prevailing in the examination room.

However, for special needs or regulatory requirements, it may be necessary that higher temperatures than room temperature, e.g., fever temperature 42° C. or even higher temperatures for desired permeation-increasing effects, should or must prevail inside donor chamber 12 and/or on the surface of the applied TTS 32 and/or on the membrane. For example, the latest FDA Draft Guideline "Transdermal and Topic Delivery Systems-Product Development and Quality Considerations" of November 2019 requires, among other things, a so-called "heated skin" permeation at 42° C., without mentioning in this guideline how these 42° C. are to be produced technically. The prior art for such effects are, for example, so-called "heat packs" or the use of textile fabrics that can be heated by means of electricity, as described in WO 2016/162481. In heat packs, for example, heat generation can be obtained by a chemical reaction of atmospheric oxygen with pyrophoric iron located on activated carbon in the presence of water. Other head pack systems release their heat as chemically released heat of crystallization after recrystallization from a supersaturated solution. However, the duration of heat generation of such heat pack systems is limited in time (<24 hours, usually not longer than 24 hours) due to the completion of a chemical reaction and is therefore not suitable for vitro permeation studies, which should go over a period of at least 24 hours. Another disadvantage of these systems is their size, here specifically the height or thickness, which does not guarantee a liquid-tight seal between the donor and acceptor chambers.

The system described in WO 2016/162481 A1 is not subject to time limitations, but insufficient heat transfer occurs or acceptable heat transfer can only be implemented at great expense.

SUMMARY OF THE INVENTION

It is an object of the invention to provide a temperature control system for a diffusion cell, a diffusion cell, a diffusion cell system, and a method for controlling the temperature of a cell head of a diffusion cell, wherein the temperature control in the cell head of a diffusion cell is improved.

According to the invention, the object is achieved by a temperature control system for a diffusion cell as described herein, a diffusion cell according to claim 11, a diffusion system as described herein, and a method for temperature control of a cell head of a diffusion cell as described herein.

The temperature control system for a diffusion cell according to the invention is preferably a temperature control system for a vertical and/or static diffusion cell, wherein it is preferred that the diffusion cell is a FRANZ diffusion cell. Particularly preferred, the diffusion cell is designed as a 10 ml or 24 ml or 115 ml diffusion cell, wherein the ml specification defines the volume of an acceptor chamber of the diffusion cell. The temperature control system comprises a cell head, in particular designed as a donor chamber. A temperature control device is connected to the cell head. It is preferred that the connection between cell head and temperature control device is designed as a fixed connection.

Hereby it is preferred that there is at least physical contact between the cell head and the temperature control device. It is particularly preferred that the cell head and the temperature control device are connected to each other in a form-fitting and/or materially bonded manner. It is preferred that the temperature control device is integrated into the cell head. By connecting the cell head to the temperature control device, it is implemented in a particularly advantageous manner that the temperature control device, as a component of the temperature control system, can be used to directly control the temperature of the cell head, for example without manually adding temperature control agents such as heat packs. Advantageously, simpler handling is implemented. The temperature control device is configured to control the temperature of the cell head. It is particularly preferred that the temperature of a dermal dosage form, such as a TTS, preferably arranged in the cell head, can be controlled by means of the temperature control device. As an alternative or in addition to temperature control of the dermal dosage form, the temperature control device is configured in particular for temperature control of a membrane, in particular a diffusion membrane, of the diffusion cell. Here, temperature control means heating and/or cooling and/or keeping the temperature constant. It is preferred that the temperature control device is configured to generate a temperature of 37° C. to 51° C., in particular of 37° C. to 42° C. Preferably, the cell head comprises an access opening. For example, the access opening allows an arrangement of the dermal dosage form in the cell head and/or air exchange in the cell head.

In a preferred embodiment, the temperature control device is integrally connected to the cell head. It is preferred that cell head and temperature control device are manufactured together by primary shaping, in particular molding, for example injection molding. Alternatively or additionally, it is preferred that temperature control device and cell head are integrally formed by means of a forming process. Alternatively or additionally, the temperature control device is preferably integrally formed with the cell head by a separation process, in particular by drilling or milling or sawing. It is also possible that the temperature control device is connected to the cell head by means of joining processes, in particular by welding, soldering or gluing.

In a preferred embodiment, the temperature control device comprises a heat exchanger. The heat exchanger is preferably a fluid heat exchanger. In the context of this application, fluid means liquid and/or gaseous. In particular, the heat exchanger is configured such that heat is transferred between the temperature control device, preferably between a temperature control fluid of the temperature control device, and the dermal dosage form and/or the membrane. It is particularly preferred that the heat exchanger is configured such that the temperature control fluid comes into direct contact with the dermal dosage form and/or the membrane.

It is preferred that the cell head substantially comprises a hollow cylindrical shape. In particular, the base area of the hollow cylinder shape is a circle. On the other hand, it is possible that the base area is oval, rectangular, square or triangular. It is preferred that the hollow cylinder is designed to be vertical. Vertical here means a substantially vertical alignment of the hollow cylinder in the experimental space. In a preferred embodiment, the one open cylinder side is the access opening and/or the other open cylinder side is a connection side, in particular a flange-like connection side, for connection to the membrane and/or acceptor chamber of the diffusion cell.

Preferably, the cell head comprises an inlet for supplying a temperature control fluid into the cell head, in particular into the interior of the cell head. In particular, the inlet is configured to supply the temperature control fluid into the interior of a donor chamber of the cell head. Preferably, the inlet is configured such that the temperature control fluid, when being supplied, comes into contact, in particular direct contact, with a diffusion membrane of the diffusion cell and/or with a dermal dosage form, such as a TTS, preferably arranged in the cell head. The temperature control fluid is in particular a temperature control liquid. It is preferred that the cell head comprises, in addition to the inlet, an outlet for discharging the temperature control fluid, in particular from the interior of the cell head. In particular, the outlet is configured to discharge the temperature control fluid from inside a donor chamber of the cell head. Preferably, the outlet is configured such that the temperature control fluid, when being discharged, loses contact, in particular direct contact, with a diffusion membrane of the diffusion cell and/or with a dermal dosage form, such as a TTS, preferably arranged in the cell head. The inlet and preferably also the outlet represent the temperature control device of the temperature control system, wherein the temperature of the cell head is controlled by introducing temperature control fluid, in particular heated temperature control fluid, via the inlet and/or discharging it via the outlet. It is preferred that inlet and/or outlet are openings, preferably holes, in the cell head. This configuration as opening/s is/are particularly preferred if the cell head is designed as a hollow cylinder. Preferably, the opening/s is/are then implemented in the outer surface of the hollow cylinder. It is preferred that inlet and/or outlet and/or access opening are designed as separate elements, in particular as separate openings. It is particularly preferred that the cell head respectively has separately: an inlet, an outlet, and an access port.

It is preferred that inlet and/or outlet has a connecting device, in particular for coupling connection with a supply device. The supply device preferably comprises at least one line, for example a hose, and in particular consists thereof.

In a preferred embodiment, the inlet and outlet are arranged substantially opposite each other, in particular in the cell head preferably designed as a hollow cylinder. Alternatively or in addition to the opposite arrangement, it is preferred that the inlet and outlet are vertically offset from each other, particularly in configurations of the cell head as a vertical hollow cylinder. Here it is preferred that the inlet is higher or lower than the outlet. The height offset makes it particularly advantageous to implement the fluid introduction and/or discharge by means of convection.

In a preferred embodiment, the temperature control fluid comprises water, in particular consists thereof. Preferably, it is a water-alcohol mixture. It is particularly preferred that it is a water-ethylene glycol mixture. The temperature of the temperature control fluid can preferably be set as required. In particular, the temperature control fluid has a temperature between 37° C. and 51° C., preferably between 37° C. and 42° C., and particularly preferably of about 37° C. It is preferred that the temperature control fluid comprises water if a temperature above room temperature, in particular above 37° C., is to be achieved in the cell head. On the other hand, it is preferred that the temperature control fluid comprises a water-ethylene glycol mixture if a temperature below room temperature is to be achieved in the cell head. Preferably, the supply and/or discharge of temperature control fluid into the cell head, in particular at the inlet and/or outlet, can be controlled as required. It is preferred, for example, that the temperature control device has at least one, preferably variably adjustable, valve for the supply and/or discharge of temperature control fluid. Preferably, the inlet and/or outlet comprises a valve.

It is preferred that the temperature control device comprises a thermal radiator. Preferably, the thermal radiator is an IR radiator. By means of a thermal radiator connected to the cell head, it is possible to carry out direct temperature control of the dermal dosage form and/or the membrane by radiation in a particularly advantageous manner.

The temperature control system preferably comprises a temperature controller, also referred to as a thermostat. It is particularly preferred that the temperature controller is configured such that it causes, in particular automatically, a preset temperature, for example, and/or ensures a constant temperature. It is also preferred that the temperature control system comprises a thermometer. It is particularly preferred that the thermometer is arranged in the cell head. In particular, the thermometer is an IR thermometer for measuring the temperature in the cell head and/or the dermal dosage form and/or the membrane. It is preferred that the temperature controller controls at least one valve for supplying and/or discharging temperature control fluid to/from the cell head. The at least one valve is preferably arranged in the inlet and/or outlet, additionally/alternatively in supply and/or discharge lines to the cell head.

It is preferred that the cell head and/or the temperature control device comprises metal, in particular consists thereof. The metal is preferably brass and/or aluminum and/or steel and/or copper. Preferred are alloys of such metals.

The diffusion cell according to the invention is in particular a FRANZ diffusion cell. It is preferred that the diffusion cell is vertically and/or statically designed. Particularly preferred is the configuration as a 10 ml or 24 ml or 115 ml diffusion cell. The diffusion cell according to the invention comprises a temperature control system having one or several of the above-described features. An acceptor chamber is connected to the temperature control system. A membrane is arranged between the temperature control system and the acceptor chamber. Preferably, the membrane is a diffusion membrane. It is particularly preferred that the membrane comprises animal or human skin, in particular consists thereof. It is preferred that the diffusion cell is structured like a conventional FRANZ diffusion cell, but the cell head of a conventional FRANZ diffusion cell is replaced by the temperature control system described above. In particular, the acceptor chamber of the diffusion cell according to the invention corresponds to the acceptor chamber of a conventional FRANZ diffusion cell. In particular, the diffusion cell according to the invention comprises a temperature control system described above as well as the acceptor chamber and/or retaining clip and/or membrane and/or acceptor chamber temperature control device of FIG. 1 or FIG. 2.

In a preferred embodiment of the diffusion cell, the cell head and the acceptor chamber are fluid-tightly separated by the membrane. Preferably, furthermore, in the connection area of the cell head and the acceptor chamber, the interior of the cell head and the interior of the acceptor chamber are fluid-tight with respect to the environment. The above fluid tightness is preferably implemented by means of at least one seal, in particular comprising an O-ring, and/or by means of a retaining clip.

The diffusion cell system according to the invention comprises at least one temperature control system having one or more of the above features or at least one diffusion cell having one or more of the above features. It is particularly preferred that the diffusion cell system comprises at least two such temperature control systems or at least two such diffusion cells. Furthermore, the diffusion cell system comprises one, in particular a single, fluid provision device. The fluid provision device is connected to the at least one temperature control system, in particular to each of the at least two temperature control systems, in a fluid-carrying manner. The fluid connection is preferably implemented via at least one line, in particular designed as a hose. It is preferred that the fluid provision device is connected to the inlet and/or the outlet of the at least one temperature control system in a fluid-carrying manner. The fluid provision device is in particular a fluid heating and/or cooling device. It is particularly preferred that the fluid provision device is a heat exchanger. Preferably, it is thus implemented in an advantageous manner that several temperature control systems and/or diffusion cells can be supplied or that their temperature can be controlled via one provision device.

The method according to the invention is a method for controlling the temperature of a cell head of a diffusion cell. Particularly preferred it is a method for controlling the temperature of a dermal dosage form and/or a membrane in a diffusion cell. According to the invention, the method comprises the step of introducing a temperature control fluid, preferably a temperature control liquid, into the cell head, in particular into the interior of the cell head, of the diffusion cell. In particular, the cell head is a donor chamber. Preferably, the temperature control fluid is introduced directly into the interior of the donor chamber. In particular, the temperature control fluid is introduced such that the temperature control fluid comes into contact, in particular direct contact, with a diffusion membrane of the diffusion cell and/or with a dermal dosage form, such as a TTS, preferably arranged in the cell head. Preferably, the method comprises the further step of discharging the temperature control fluid from the cell head, in particular from the interior of the cell head. This step of discharging takes place in particular after and/or during the step of introducing the temperature control fluid. Preferably, when discharging, the temperature control fluid is discharged, in particular directly, from the interior of the donor chamber.

It is preferred that the method according to the invention is carried out with a temperature control system having one or more of the features described above, or a diffusion cell having one or more of the features described above, or a diffusion cell system having one or more of the features described above. In this context, it is not necessary that, in order to carry out the method with a temperature control system described above, said temperature control system comprises a cell head with a temperature control device connected thereto. For example, it is also possible withing the scope of the method that the temperature control device is separate from the cell head. Preferably, it is also possible that the method is carried out with a standard cell head, in particular a standard diffusion cell, a FRANZ diffusion cell.

The temperature control system for a diffusion cell according to the invention, the diffusion cell according to the invention, the diffusion cell system according to the invention, as well as the method according to the invention for controlling the temperature of a cell head of a diffusion cell, results in particular in the advantages of improved temperature control in the cell head, preferably in the sense of a more reliable and/or more constant and/or not time-limited temperature control compared to prior art.

In the following, the invention is described in more detail by means of preferred embodiments with reference to the accompanying drawings.

DESCRIPTION OF THE INVENTION

Figure 1:
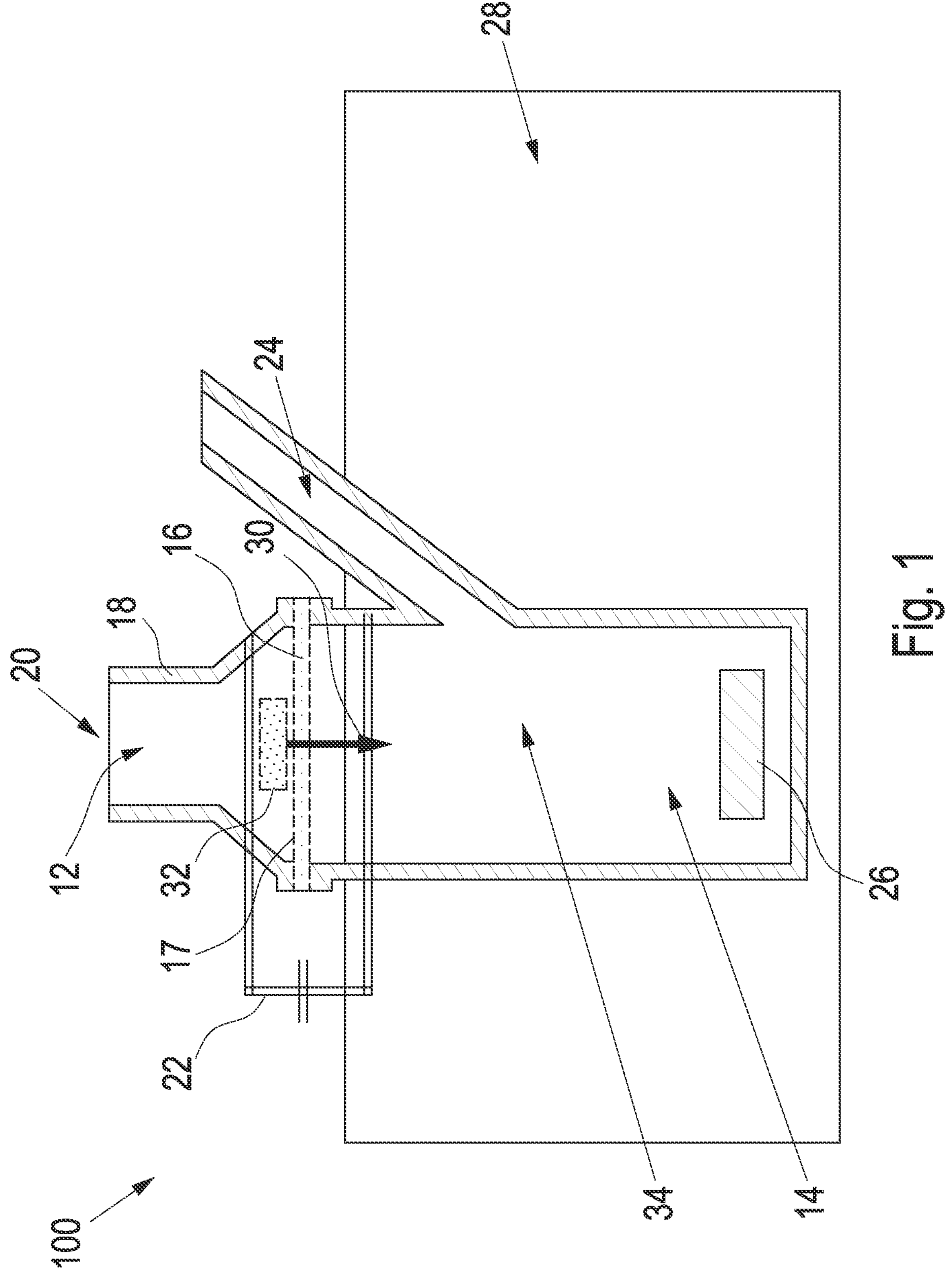
FIG. 1 is a schematic sectional view of an embodiment of a diffusion cell according to prior art.

In the Figures, similar or identical components or elements are identified by the same reference numerals or variations thereof (e.g. 10, 10*a* and 10*b*). In particular in the interest of improved clarity, preferably elements already identified are not provided with reference numerals in all Figures.

Figure 2:
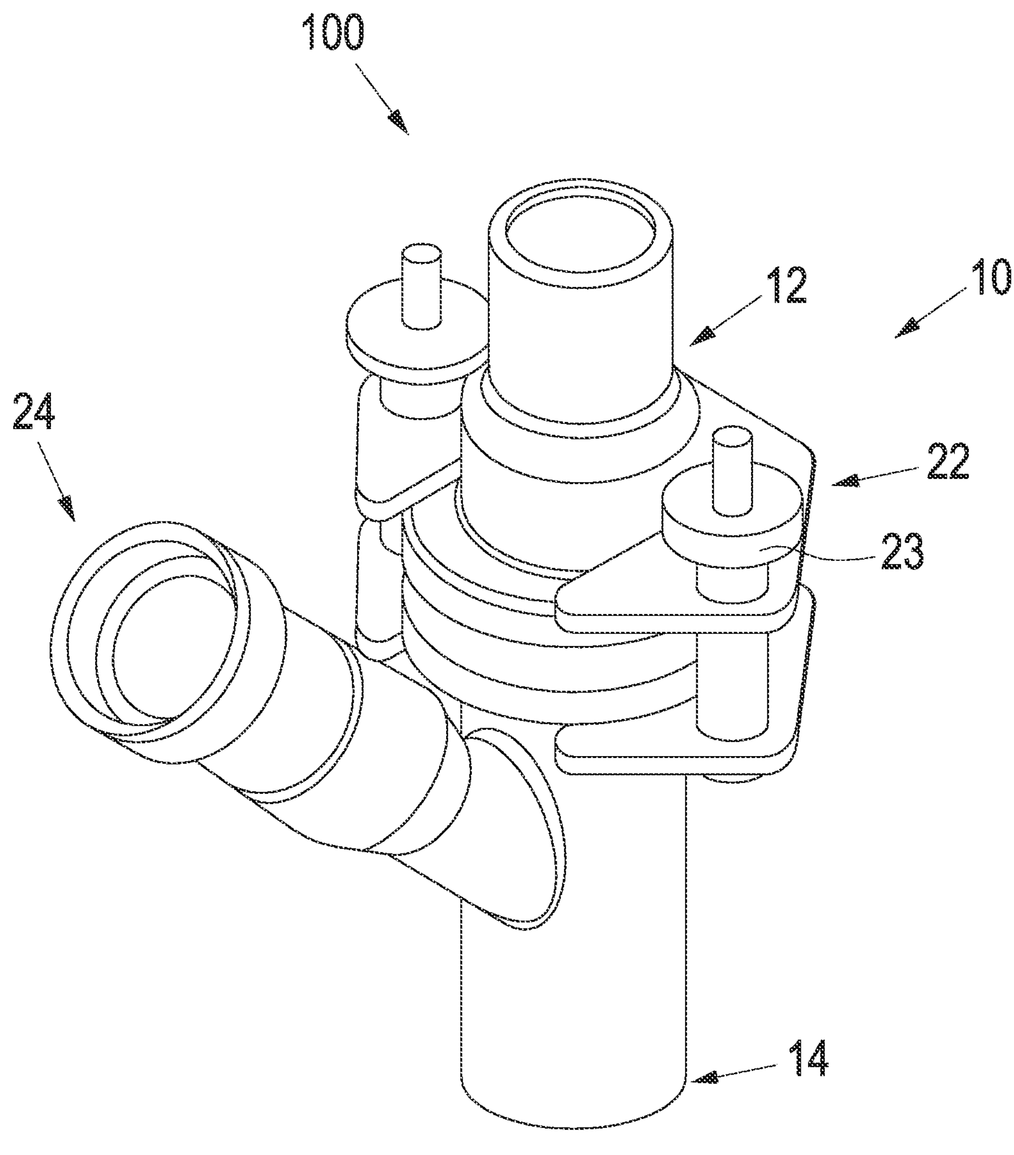
FIG. 2 is a perspective view of an embodiment of a diffusion cell according to prior art.

FIGS. 1 and 2 were already explained above.

Figure 3:
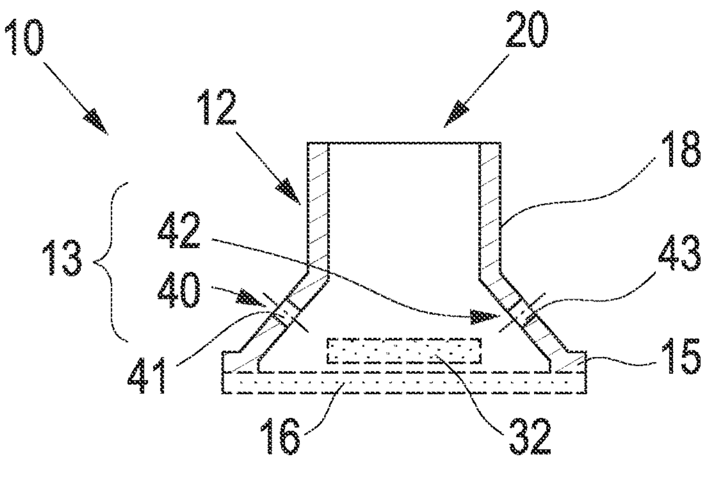
FIGS. 3 to 5 are schematic sectional views of several embodiments of a temperature control system according to the invention.

FIG. 3 is a sectional view of a temperature control system 10 according to the invention.

The temperature control system 10 shown is preferably a temperature control system for a vertical and/or static diffusion cell, for example for a FRANZ diffusion cell. In particular, the temperature control system 10 may be combined with an acceptor chamber 14 according to FIG. 1 or FIG. 2, and/or a retaining clip 22 according to FIG. 1 or FIG. 2, to form a diffusion cell. The temperature control system of FIG. 3 is substantially based on the corresponding embodiment shown of FIG. 1, however, the features according to the invention described below have been implemented.

The temperature control system of FIG. 3 comprises a cell head 12 which is formed here as a donor chamber. The cell head 12 substantially has the form of a hollow cylinder 18, wherein hollow cylinder 18 has, in the manner shown, a cylindrical shape in the upper area with a circular base area and a constant diameter. Moving downward, the diameter of hollow cylinder 18 increases and terminates with a flange device 15 for connection to a membrane 16 and/or an acceptor chamber 14 (see e.g. FIG. 1). In the upper area, cell head 12 has an access opening 20.

It is illustrated that cell head 12 of temperature control system 10 is connected to a membrane 16 on which, within the donor chamber, a dental dosage form in the form of a TTS 32 is arranged.

According to the invention, cell head 12 is connected to a temperature control device 13, wherein an integral connection is shown. The temperature control device 13 comprises a fluid inlet 40 and a fluid outlet 42. The fluid inlet 40 is designed as a hole 41 and fluid outlet as a hole 43 in hollow cylinder 18 of cell head 12. Inlet 40 and outlet 42 are shown opposite each other and arranged at the same vertical height. However, it is also possible for inlet 40 and outlet 42 to have a different arrangement, for example, instead of being arranged 180° C. opposite each other, they may only have a 90° C. arrangement, etc. Alternatively or additionally, a height offset between inlet and outlet 42 is also possible. Here, a height offset means in particular that an inlet 40 and an outlet 42 are arranged in different, preferably parallel, particularly preferably truly parallel, cross-sectional planes of hollow cylinder 18. On the other hand, it is also possible to design the inlet and the outlet as a single opening.

Figure 7:
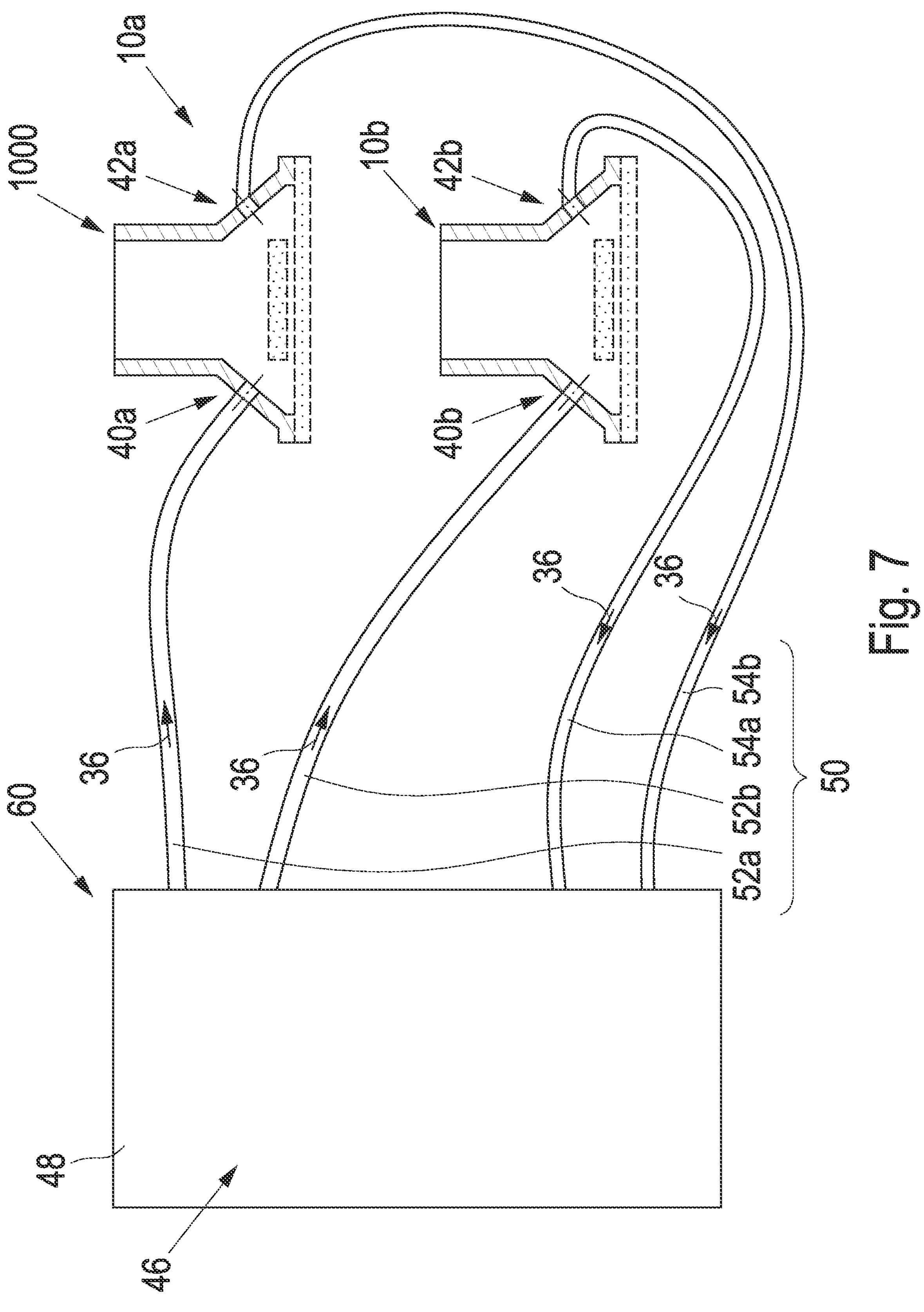
FIG. 7 is a schematic view of an embodiment of a diffusion cell system according to the invention.

A temperature control fluid 36 can be introduced into the donor chamber through inlet 40, wherein temperature control fluid 36 can be discharged from the donor chamber through outlet 42 (see, e.g. FIG. 7). Preferably, temperature control fluid 36 is introduced into the interior of the donor chamber through inlet 40 so that, in particular, there is direct contact between temperature control fluid 36 and membrane 16 and/or the dental dosage form. It is preferred that temperature control fluid 36 is discharged through outlet 42 from the interior of the donor chamber. Preferably, the temperature control fluid is a temperature control liquid, in particular a liquid comprising water. The liquid preferably has a temperature, in particular a constant temperature, for temperature control for the donor chamber, particularly preferably a temperature control of membrane 16 and/or the dermal dosage form 32 is effected thereby. It is preferred that the temperature control fluid has a temperature of 37° C. to 51° C., in particular of 37° C. to 42° C. In FIG. 3, inlet 40 and outlet 42 are designed as simple holes 41, 43. However, other embodiments are also possible. For example, it is possible that inlet 40 and/or outlet 42 comprises a connection device, in particular for coupling connection with a (not shown) supply device, in particular a line, preferably a hose.

Figure 4:
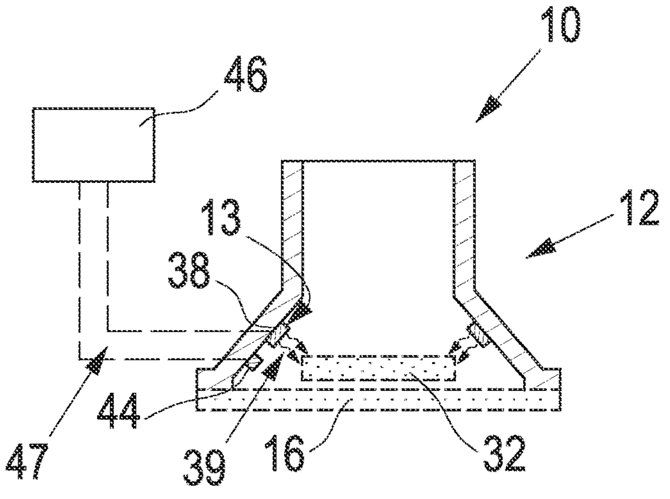

FIG. 4 shows a further embodiment of a temperature control system 10 according to the invention, the embodiment being based on that of FIG. 3. Instead of temperature control device 13 with inlet 40 and outlet 42 of FIG. 1, the embodiment of FIG. 4 comprises a temperature control device 13 with thermal radiator 38. The thermal radiator may be a heating, for example. It is preferred that thermal radiator 38 is an IR radiator that emits IR rays for temperature control of cell head 12, in particular membrane 16 and/or dermal dosage form 32.

Furthermore, temperature control system 10 of FIG. 4 comprises a thermometer 44. Thermometer 44 is particularly designed as an IR thermometer. It is preferred that thermometer 44 detects the temperature inside cell head 12. It is particularly preferred that thermometer 44 detects the temperature of the dermal dosage form and/or membrane 16. Temperature control device 13 and thermometer 44 are connected to a temperature controller 46 via a data-transmitting connection device 47. For example, the data transmission device 47 may be a wired and/or wireless connection. Preferably, temperature controller 46 is configured to control the temperature of the cell head. Here, it is particularly preferred that temperature controller 46 detects an actual temperature by means of a thermometer 44 and regulates this temperature to a set temperature, in particular a preset temperature, with the aid of temperature control device 13.

Figure 5:
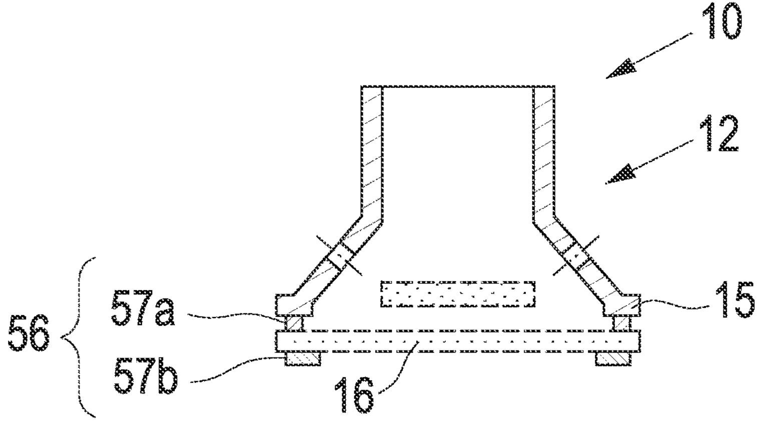

FIG. 5 shows a further embodiment of a temperature control system 10 according to the invention, wherein temperature control system 10 of FIG. 5 is substantially based on the embodiment of FIG. 3.

A seal 56 is provided to connect cell head 12 to an acceptor chamber 14 (not shown) and membrane 16 in order to form a diffusion cell 100 (not shown). It is illustrated that seal 56 comprises an O-ring 57*a* for connection between cell head 12 and membrane 16 as well as another O-ring 57*b* for connection of membrane 16 and acceptor chamber 14. On the other hand, it is possible to provide only one of the two O-rings 57*a* or 57*b*.

Figure 6:
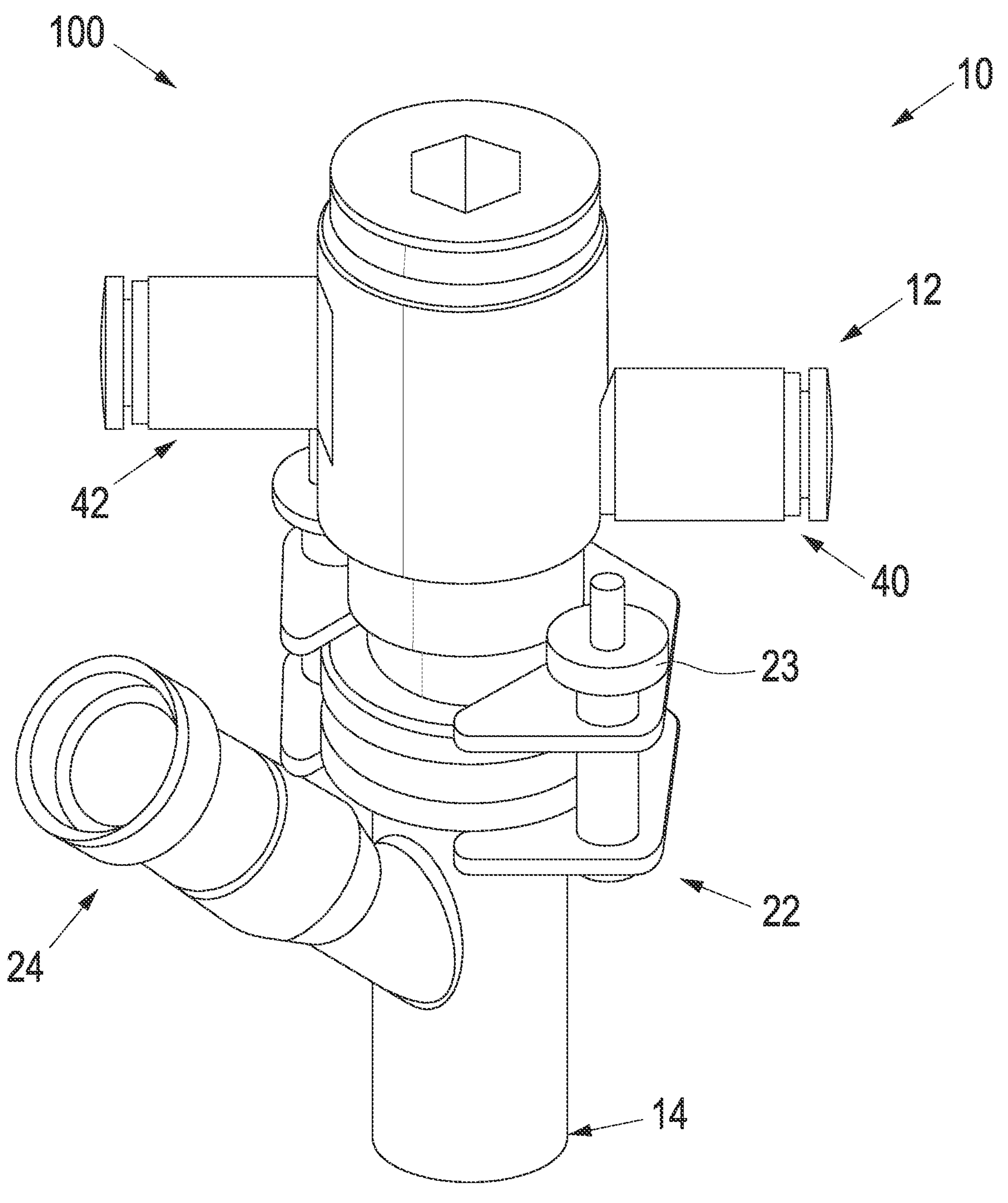
FIG. 6 is a perspective view of an embodiment of a diffusion cell according to the invention with a further embodiment of a temperature control system according to the invention.

FIG. 6 shows an embodiment of a diffusion cell 100 according to the invention with a further embodiment of a temperature control system 10 according to the invention.

Temperature control system 10 of FIG. 1 comprises a cell head with an inlet 40 and an outlet 42 opposite each other, wherein these are arranged vertically offset from each other.

The remaining embodiment of diffusion cell 100 of FIG. 6 corresponds in particular substantially to the configuration of FIG. 2 (without cell head 12 illustrated there).

FIG. 7 shows an embodiment of a diffusion cell system 1000 according to the invention with two embodiments of temperature control systems 10*a*, 10*b* according to the invention. Here, the temperature control systems 10*a*, 10*b* are based in particular on the embodiment shown in FIG. 3.

The temperature control systems 10*a*, 10*b* are connected via the respective inlets 40*b* to fluid-carrying inlet lines 52*a*, 52*b* for fluid introduction, and via outlets 42*a*, 42*b* to outlet lines 54*a*, 54*b* for fluid discharge. The lines 52*a*, 52*b*, 54*a*, 54*b* are preferably hoses, so that together they form a hose connection 50. As an example, the flow of temperature control fluid 36 is shown with arrows. Temperature control fluid 36 is in particular a temperature control liquid, preferably comprising water.

In the illustrated form, temperature control fluid 36 is provided by a fluid provision device 60. It is preferred that fluid provision device 60 comprises a heat exchanger 48 and/or a temperature controller 46 for, in particular controlled, temperature control of the temperature control systems 10*a*, 10*b*.

It is particularly preferred that the embodiments of the temperature control system according to the invention, in particular those described above, are configured such that they can be integrated into standard FRANZ diffusion cells 100 (see e.g. FIGS. 1 and 2) in order to form the respective cell head 12 of diffusion cell 100, wherein the standard cell head 12 is replaced by temperature control system 10 according to the invention.

Experimental tests were performed to evaluate the invention and are described below.

1. Preparation of Skin for In Vitro Permeation Studies

Human skin dermatomized to 500 μm (example Na-diclofenac) as well as to 800 μm (example nicotine), which was obtained as post-operative skin from a cosmetic surgery clinic, was used as the skin model for membrane 16. The skin was dermatomized or sectioned to the appropriate layer thicknesses using an electric battery dermatome Acculan 3TI (Aesculap AG, Tuttlingen, Germany). From this prepared donor skin (abdomen, female, age 50 years for Na-diclofenac as well as abdomen, female, age 60 years for nicotine), circular punched blanks with a diameter of 25 mm were punched out and stored sealed in PE bags at −20° C. (maximum storage time at these conditions up to 16 months) until further use.

2. Conducting the In Vitro Permeation Studies

The permeation studies were performed exemplarily in a static and vertical diffusion cell 100 designed as a Franz cell (Glastechnik Gräfenroda, Germany) with a diffusion area of 1.595 cm 2 and an acceptor volume of 10 ml. The diffusion cell 100 used according to the invention corresponds to that shown in FIG. 6, wherein a standard diffusion cell 100 according to FIG. 2 was used as a reference. Phosphate buffer with a pH value of 5.5 according to DAB 10 and with an addition of 0.1% sodium azide as a bactericidal preservative was used as acceptor medium 24, tempered at 32° C. throughout the entire permeation period and stirred continuously for uniform mixing of the permeated active ingredient. At the scheduled sampling times, the acceptor medium was completely replaced with a fresh one. After applying the TTS 32 to the epidermal side of the skin punched blanks 15, it was then placed on glass rim 102 of the cell base, acceptor chamber 14 and the Franz cells. The dermal side of the TTS points to the acceptor chamber. The temperature control system 10 (FIG. 6) and a standard cell head of a Franz cell (FIG. 2) used as a reference were placed on top of this. By means of a corresponding retaining clip 12, both cell chambers 12, 14 of both systems were sealed liquid-tight and finally each was filled with acceptor medium 34.

3. Analytical Determination of Na-Diclofenac in the Acceptor Samples

The analytical determination was carried out by HPLC on a special acid- and base-deactivated Zorbax C8 separation column (150×4.6 mm, 5 μm particle size; VDS Optilab, Berlin) using UV detection at 225 nm and at 30° C. separation column temperature. A 50:50 (v %/v %) mixture consisting of acetonitrile and 0.025 m sodium dihydrogen phosphate solution adjusted to a pH value of 3.2 was used as an eluent. The flow rate was 1.5 ml/min and 50 μl was injected. The quantitative evaluation was performed using an external reference standard.

4. Analytical Determination of Nicotine in the Acceptor Samples

The analytical determination was carried out by HPLC on a special graphite separation column HyperCarb (150×4.6 mm, 5 μm particle size; Thermo Fischer, Berlin) using UV detection at 258 nm and at 40° C. separation column temperature. A mixture consisting of acetonitrile, HPLC water and triethylamine 20:80:0.1 (v %/v %/v %) was used as an eluent. The flow rate was 1.2 ml/min and 50 μl was injected. The quantitative evaluation was performed using an external reference standard.

5. Result

Figure 8:
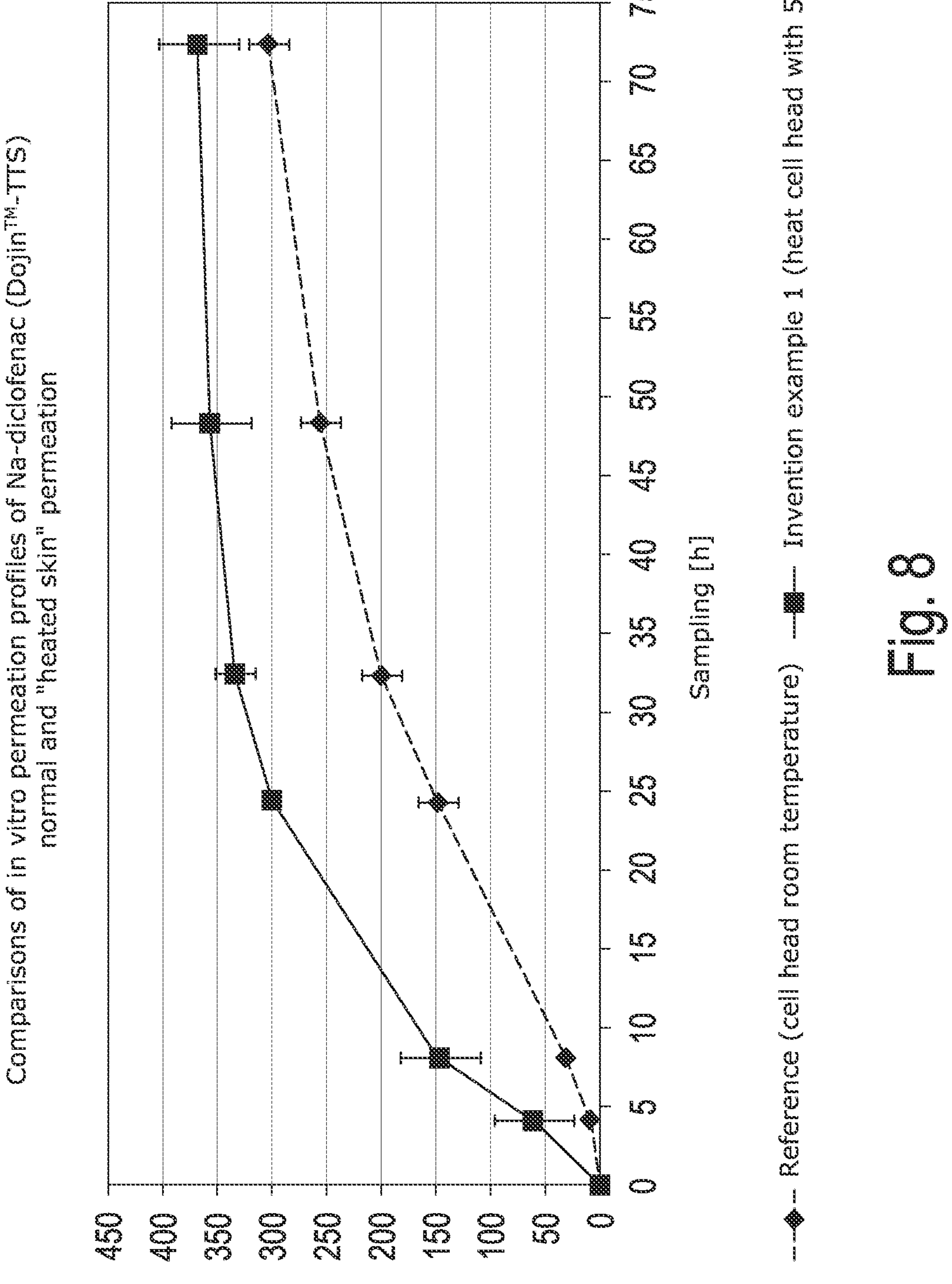
FIGS. 8 and 9 are illustrations von comparative results of experimental tests of temperature control systems according to the invention with prior art.
Figure 9:
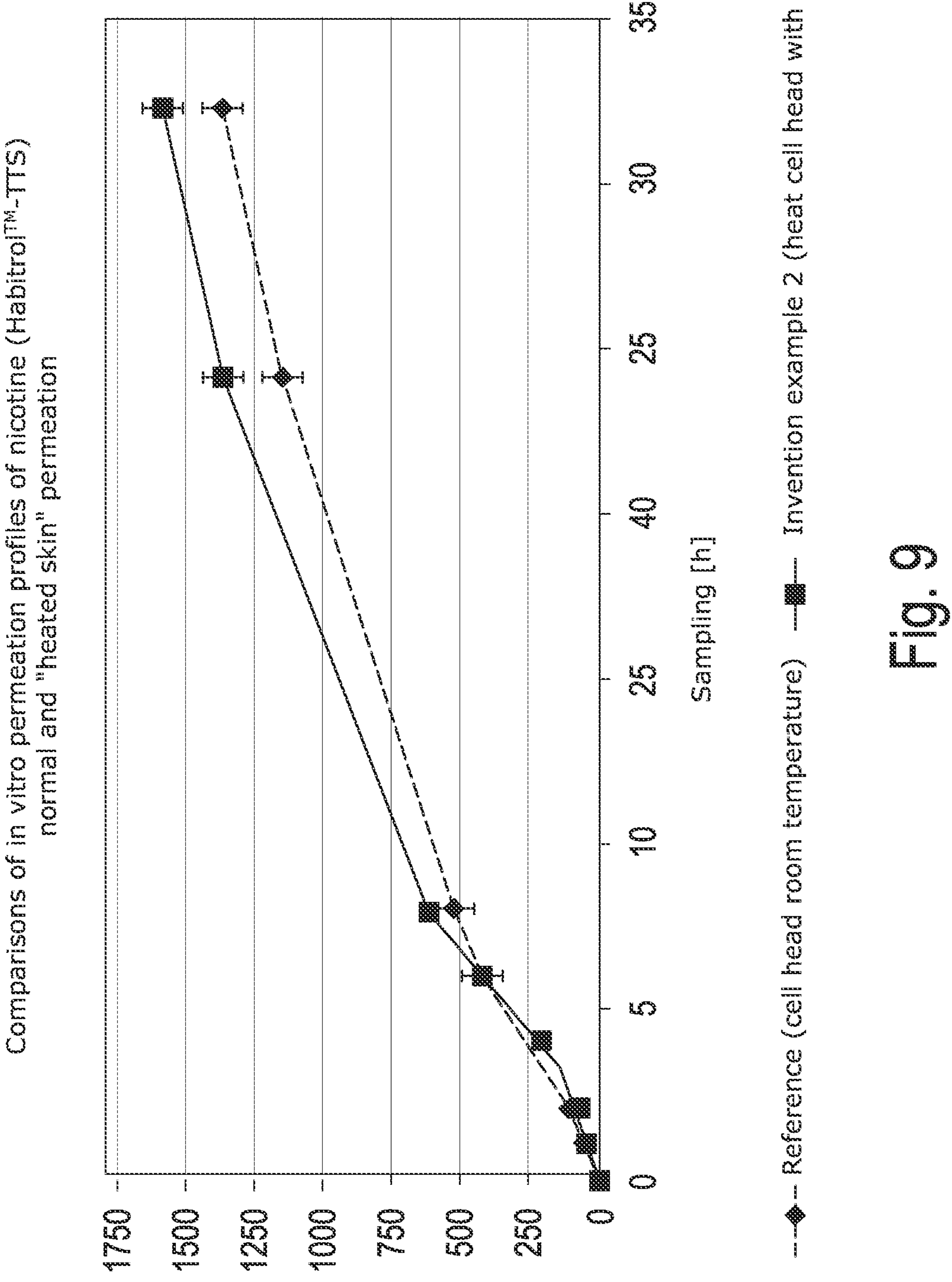

The comparative results of the experiments are shown in FIGS. 8 and 9.

Here, FIG. 8 shows a comparison of the permeation profile of the embodiment according to the invention with the permeation profile of a standard FRANZ diffusion cell as a reference using the example of an in vitro permeation with Na-diclofenac (Dojin™ TTS).

It can be determined that the release quantity or release rate of the embodiment according to the invention is statistically significantly larger by a factor of about 2 compared with the reference after 24 hours (corresponding approximately to the usual wearing time).

FIG. 9 shows a comparison of the permeation profile of the embodiment according to the invention with a standard FRANZ diffusion cell as a reference using the example of in vitro permeation with nicotine (Habitol™ TTS).

Here it results that the release quantity or release rate of the embodiment according to the invention is statistically significantly larger by a factor of about 1.2 compared to the reference after 24 hours. It can also be seen that due to the lower cell head temperature of 42° C. compared to the experiment in FIG. 8 with 51° C., there is a lower degree of increase in permeated quantity.

Thus, the experiments demonstrate the advantageous function of the present invention.

The invention claimed is:

1. A temperature control system for a vertical and static diffusion cell that can be fluidically connected to a membrane, the system comprising:

a donor chamber; and a temperature control device, wherein the temperature control device comprises an inlet into the donor chamber for supplying a temperature control fluid having a temperature of 37° C. to 51° C. into an interior portion of the donor chamber, and wherein the temperature control device does not comprise a fluid jacket.

2. The temperature control system according to claim 1, wherein the temperature control device is integrally formed with the donor chamber.

3. The temperature control system according to claim 1, wherein the temperature control device comprises a fluid heat exchanger.

4. The temperature control system according to claim 1, wherein the donor chamber has a hollow cylindrical shape.

5. The temperature control system according to claim 1, wherein the donor chamber further comprises an outlet for discharging the temperature control fluid from the interior portion of the donor chamber.

6. The temperature control system according to claim 5, wherein the fluid inlet and outlet of the donor chamber are arranged opposite or vertically offset from one another.

7. The temperature control system according to claim 1, wherein the temperature control fluid comprises water.

8. The temperature control system according to claim 7, wherein the temperature control fluid further comprises alcohol mixed with the water.

9. The temperature control system according to claim 7, wherein the temperature control fluid further comprises ethylene glycol mixed with the water.

10. The temperature control system according to claim 1, comprising a temperature controller or a thermometer.

11. The temperature control system according to claim 1, wherein the donor chamber comprises metal.

12. The temperature control system according to claim 11, wherein the donor chamber comprises brass, aluminum, steel, or copper.

13. A diffusion cell comprising:

a temperature control system according to claim 1;

an acceptor chamber connected to the temperature control system; and the membrane, wherein the membrane is arranged between the temperature control system and the acceptor chamber.

14. The diffusion cell according to claim 13, wherein the donor chamber and the acceptor chamber are separated from each other in a fluid-tight manner via the membrane.

15. A diffusion cell system comprising:

a diffusion cell according to claim 13; and a fluid provision device, wherein the fluid provision device is connected to the at least one temperature control system in a fluid-carrying manner.

16. The diffusion cell according to claim 13, wherein the donor chamber and the acceptor chamber are separated from each other in a fluid-tight manner by means of at least one seal or a retaining clip, via the membrane.

17. The diffusion cell according to claim 13, wherein the donor chamber and the acceptor chamber are separated from each other in a fluid-tight manner via the membrane, and wherein the membrane is located in a connection area of the donor chamber and the acceptor chamber.

18. The diffusion cell according to claim 13, wherein the temperature control fluid is supplied into the interior portion of the donor chamber such that the temperature control fluid comes into direct contact with the membrane.

19. A diffusion cell system comprising:

at least one temperature control system according to claim 1; and a fluid provision device, wherein the fluid provision device is connected to the temperature control system in a fluid-carrying manner.

20. A method for controlling the temperature of a donor chamber of a diffusion cell, the method comprising the following step:

introducing a temperature control fluid having a temperature of 37° C. to 51° C. into the donor chamber of the diffusion cell of claim 1 so as to control the temperature of an interior portion of the donor chamber.

21. The temperature control system according to claim 1, wherein the temperature control fluid is provided by a fluid provision device, and wherein the fluid provision device comprises a heat exchanger or a temperature controller for temperature control to a temperature of 37° C. to 51° C. of the temperature control fluid being supplied through the inlet.

22. The temperature control system according to claim 1, wherein when the donor chamber is fluidically connected to the membrane, and wherein the temperature control fluid is supplied into the interior portion of the donor chamber such that the temperature control fluid comes into direct contact with the membrane.

23. A temperature control system for a vertical and static diffusion cell that can be fluidically connected to a membrane, the system comprising:

a donor chamber comprising an inlet and an outlet; and a heat exchanger fluidically connected to the inlet and the outlet and forming a fluid circuit, wherein the fluid circuit supplies a temperature control fluid having a temperature of 37° C. to 51° C. into an interior portion of the donor chamber, and wherein temperature control fluid is located only within the fluid circuit.

* * * * *